(12) United States Patent
Schmidt

(10) Patent No.: US 7,420,098 B2
(45) Date of Patent: Sep. 2, 2008

(54) DUAL ZONE AROMATIC ALKYLATION PROCESS

(75) Inventor: Robert J. Schmidt, Barrington, IL (US)

(73) Assignee: UOP LLC, Des Plaines, IL (US)

( * ) Notice: Subject to any disclaimer, the term of this patent is extended or adjusted under 35 U.S.C. 154(b) by 68 days.

(21) Appl. No.: 11/622,937

(22) Filed: Jan. 12, 2007

(65) Prior Publication Data

US 2008/0171900 A1 Jul. 17, 2008

(51) Int. Cl.
*C07C 2/66* (2006.01)

(52) U.S. Cl. ........................ 585/449; 585/467
(58) Field of Classification Search ............... 585/449, 585/467
See application file for complete search history.

(56) References Cited

U.S. PATENT DOCUMENTS

| 2,620,314 | A | 12/1952 | Hoekstra |
| 3,308,069 | A | 3/1967 | Wadlinger et al. |
| RE28,341 | E | 2/1975 | Wadlinger et al. |
| 4,008,290 | A | 2/1977 | Ward |
| 4,774,377 | A | 9/1988 | Barger et al. |
| 4,891,458 | A | 1/1990 | Innes et al. |
| 5,081,323 | A | 1/1992 | Innes et al. |
| 5,522,984 | A | 6/1996 | Gajda et al. |
| 5,672,799 | A | 9/1997 | Perego et al. |
| 5,723,710 | A | 3/1998 | Gajda et al. |
| 6,756,030 | B1 | 6/2004 | Rohde et al. |
| 6,835,862 | B1 | 12/2004 | Gajda et al. |
| 6,936,744 | B1 | 8/2005 | Cheng et al. |
| 2006/0224031 | A1 | 10/2006 | Jan et al. |

FOREIGN PATENT DOCUMENTS

| EP | 432814 A1 | 6/1991 |
| WO | WO 97/33830 | 9/1997 |

*Primary Examiner*—Thuan Dinh Dang
(74) *Attorney, Agent, or Firm*—David J Piasecki

(57) ABSTRACT

A process for the catalytic alkylation of an aromatic substrate with an alkylating agent is disclosed that comprises contacting the aromatic substrate and the alkylating agent in sequential alkylation zones to obtain an alkylaromatic. The first catalyst comprises UZM-8 zeolite and the second catalyst comprises beta zeolite. The process is particularly well suited for the alkylation of benzene with propylene to produce cumene.

20 Claims, No Drawings

DUAL ZONE AROMATIC ALKYLATION PROCESS

TECHNICAL FIELD

A process for producing monoalkylated aromatic compounds by alkylation is disclosed. More specifically, a highly-selective alkylation for producing cumene and ethylbenzene is disclosed using dual alkylation zones with different catalysts.

BACKGROUND

Alkylation of aromatic compounds with a $C_2$ to $C_4$ olefin and transalkylation of polyalkylaromatic compounds are two common reactions for producing monoalkylated aromatic compounds. Examples of these two reactions that are practiced industrially to produce cumene (isopropylbenzene) are the alkylation of benzene with propylene and the transalkylation of benzene and a diisopropylbenzene (DIPB). The alkylation reaction forms cumene and common byproducts such as DIPBs and triisopropylbenzenes (TIPBs). DIPBs, TIPBs, and some of the higher polyisopropylbenzenes can be readily transalkylated by benzene to produce cumene. Combining alkylation and transalkylation in a process can thus maximize cumene production. Such combinations can have two reactions zones, one for alkylation and the other for transalkylation, or a single reaction zone in which both alkylation and transalkylation occur.

A key operating variable in alkylation and transalkylation reactions to produce a monoalkylated aromatic is the molar ratio of aryl groups per alkyl group. The numerator of this ratio is the number of moles of aryl groups passing through the reaction zone during a specified period of time. The number of moles of aryl groups is the sum of all aryl groups, regardless of the compound in which the aryl group happens to be. In cumene production, for example, one mole of benzene, one mole of cumene, and one mole of DIPB each contribute one mole of aryl group to the sum of aryl groups. The denominator of this ratio is the number of moles of alkyl groups that have the same number of carbon atoms as that of the alkyl group on the desired monoalkylated aromatic and which pass through the reaction zone during the same specified period of time. The number of moles of alkyl groups is the sum of all alkyl and alkenyl groups with the same number of carbon atoms as that of the alkyl group on the desired monoalkylated aromatic, regardless of the compound in which the alkyl or alkyl group happens to be, except that paraffins are not included. In cumene production, the number of moles of propyl groups is the sum of all propyl and propenyl groups, regardless of the compound in which the propyl or propenyl group happens to be, except that paraffins, such as propane, n-butane, isobutane, pentanes, and higher paraffins are excluded from the computation of the number of moles of propyl groups. For example, one mole of propylene and one mole of cumene each contribute one mole of propyl group to the sum of propyl groups, whereas one mole of DIPB contributes two moles of propyl groups and one mole of TIBP contributes three moles of propyl groups. Hexylbenzene and nonylbenzene contribute no moles of propyl groups. Another related operating variable in alkylation reactions to produce a monoalkylated aromatic is the molar ratio of aromatic substrate per alkylating agent, and in cumene production the numerator of this molar ratio is the moles of benzene and the denominator is the moles of propylene.

Many catalysts containing zeolites have been proposed and used for alkylating and transalkylating aromatics. Regardless of whether the reaction is alkylation or transalkylation, it is of critical importance that the zeolitic catalyst exhibits not only the capability to initially perform its specified functions, but also that it has the capability to perform them satisfactorily for prolonged periods of time. The analytical terms used in the art to measure how well a particular catalyst performs its intended functions in a particular hydrocarbon reaction environment are activity, selectivity, and stability. And for purposes of discussion here, these terms are conveniently defined for a given charge stock as follows: (1) "activity" is a measure of the catalyst's ability to convert hydrocarbon reactants into products at a specified severity level, where severity level means the conditions used—that is, the temperature, pressure, contact time, concentration of reactants, and presence of diluents such as paraffins; (2) "selectivity" refers to the amount of desired product or products obtained relative to the amount of reactants charged or converted; and (3) "stability" refers to the rate of change with time of the activity and selectivity parameters—obviously, the smaller rate implying the more stable catalyst.

In a process for producing cumene, for example, activity commonly refers to the amount of conversion of propylene that takes place at a specified severity level and is typically measured by olefin content of the alkylation reactor effluent; selectivity refers to the amount of cumene yield, relative to the amount of the propylene consumed that is obtained at the particular activity or severity level; and stability is typically equated to the rate of change with time of activity, as measured by the position of the maximum temperature (due to the exothermic reaction) in the catalyst bed after a suitable interval of time.

However, when a continuous alkylation process is run to produce a constant olefin conversion, the severity level is continuously adjusted by adjusting the conversion temperature in the reaction so that the rate of change of activity finds response in the rate of change of conversion temperatures while changes in the position of the exotherm are customarily taken as indicative of activity stability. Alternatively, additional catalyst may be used to compensate for any activity instability such that the change in position of the exotherm is allowed to proceed through the catalyst bed without changing reaction temperature until such time that olefin breakthrough occurs. At the time of breakthrough, action must be taken to either increase operating temperature to make up for the loss in activity or the catalyst must be regenerated to recover lost activity. Stability is also often typically equated to the rate of change with time of yield, as measured by cumene yield.

Accordingly, a major problem facing workers in this area of the alkylation art is the development of selective catalytic systems that have activity-stability and yield-stability. Zeolites that have been proposed and/or used for alkylating aromatics include beta, UZM-8, and other zeolites including Y, ZSM-5, PSH-3, MCM-22, MCM-36, MCM-49, and MCM-56. In response to the hydrocarbon processing industry's demands for lower molar ratios of aryl groups per alkyl group and more efficient utilization of feed olefins, improved processes for the production of alkylaromatics are sought.

SUMMARY OF THE DISCLOSURE

A process for the catalytic alkylation of an aromatic substrate with an alkylating agent is disclosed that comprises contacting the aromatic substrate and the alkylating agent in sequential alkylation zones to obtain an alkylaromatic. The first catalyst comprises UZM-8 zeolite and the second catalyst comprises beta zeolite. This process is based on the discovery that this combination of zeolite catalysts in a sequential configuration shows surprising improvements in selectivity, activity-stability, and selectivity-stability relative to the prior art. The process disclosed herein is particularly well-suited for operating at high severity operating, including lower molar ratios of aryl groups per alkyl group and high alkylating agent space velocities, as well as at high water concentrations.

Accordingly, in one embodiment, the process disclosed herein is directed to alkylating an aromatic feedstock with an alkylating agent. The aromatic feedstock and the alkylating agent are contacted with a first catalyst comprising UZM-8 zeolite in a first alkylation zone at first alkylation conditions to obtain a first effluent. The first effluent is contacted with a second catalyst comprising beta zeolite in a second alkylation zone at second alkylation conditions to obtain a second effluent comprising an alkylaromatic. More specifically, the aromatic substrate can be benzene, the olefin can be ethylene or propylene, and the alkylaromatic can be ethylbenzene or cumene.

DETAILED DESCRIPTION OF THE PRESENTLY PREFERRED EMBODIMENTS

The process disclosed herein can be expected to be applicable generally to the alkylation of an alkylation substrate with an alkylation agent. The process disclosed herein is more specifically applicable to the production of an alkyl aromatic by alkylation of a feed aromatic with a feed olefin. Although benzene is the principal feed aromatic of interest, feed aromatics such as alkyl-substituted benzenes, condensed ring systems generally, and alkylated derivatives thereof may be used. Examples of such feed aromatics are toluene, ethylbenzene, propylbenzene, diisopropylbenzene and so forth; xylene, mesitylene, methylethylbenzene, and so on; naphthalene, anthracene, phenanthrene, methylnaphthalene, dimethyl-naphthalene, and tetralin. Any alkyl groups present as substituent groups on the feed aromatic typically contain from 1 to 8 carbon atoms per group, preferably from 1 to 4 carbon atoms per group. More than one feed aromatic can be used. The feed aromatic may be introduced into an alkylation catalyst bed in one or more aromatic feed stream. Each aromatic feed stream may contain one or more feed aromatics. Besides the feed aromatic(s), an aromatic feed stream may contain non-aromatics, including but not limited to saturated and unsaturated cyclic hydrocarbons that have the same, one more, or one less, number of carbon atoms as the feed aromatic. For example, an aromatic feed stream containing benzene may also contain cyclopentane, cyclohexane, cycloheptane, cyclopentenes, cyclohexenes, or cycloheptenes, as well as methylated versions of any of these hydrocarbons, or mixtures thereof. The concentration of each feed aromatic in each aromatic feed stream may range from 0.01 to 100 wt %. Sources of benzene, toluene, xylene, and or other feed aromatics include product streams from naphtha reforming units, aromatic extraction units, and petrochemical complexes for the producing para-xylene and other aromatics.

Feed olefins containing from 2 to 6 carbon atoms are the principal alkylating agents contemplated for the process disclosed herein. Examples of such feed olefins include $C_2$-$C_4$ olefins, namely ethylene, propylene, butene-1, cis-butene-2, trans-butene-2, and isobutene. However, feed olefins having from 2 to 20 carbon atoms may be used effectively in the process disclosed herein. More than one feed olefin may be used. The feed olefin may be introduced into an alkylation catalyst bed in one or more olefinic feed streams. Each olefinic feed stream may contain one or more feed olefins. In addition to the feed olefin(s), an olefinic feed stream may contain non-olefins, such as paraffins that have the same number of carbon atoms as the olefin. For example, a propylene-containing olefinic feed stream may also contain propane, while an olefinic feed stream containing ethylene may also contain ethane. The concentration of each feed olefin in each olefinic feed stream may range from 0.01 to 100 wt %. Sources of olefinic feed streams containing mixtures of olefins include refinery FCC propane/propylene streams, naphtha cracking unit off gases, gas plant off gases, and other refinery streams.

The basic configuration of a catalytic aromatic alkylation process is known in the art. The feed aromatic and the feed olefin are preheated and charged to an alkylation zone containing generally from one to four reactors in series. Suitable cooling means may be provided between reactors to compensate for the net exothermic heat of reaction in each of the reactors. Suitable means may be provided upstream of or with each reactor to charge additional feed aromatic, feed olefin, or other streams (e.g., effluent of a reactor, or a stream containing one or more polyalkylbenzenes) to any reactor in the alkylation zone. Each alkylation reactor may contain one or more alkylation catalyst beds. Vessels or enclosures that can function as suitable reactors are known in the art. Common configurations of an alkylation zone include: one reactor with four catalyst beds; two reactors, each of which has two catalyst beds; and one reactor with four catalyst beds and a second reactor with two catalyst beds. The number of reactors is generally less than eight, and the number of catalyst beds in a given reactor is generally less than six.

The first and second alkylation zones respectively contain the first and second alkylation catalysts. Each zone typically comprises a separate reactor, for example with the first alkylation zone comprising a first reactor and the second alkylation zone comprising two subsequent reactors. However, it is possible that the alkylation zones could be separate beds in a single vessel or enclosure. Each alkylation zone may be comprise two or more reactors with suitable cooling means or means for introducing streams provided between reactors. The segregated alkylation zones also may be separated by one or more reaction zones containing a catalyst composite having a different composition from either of the catalyst composites of the process disclosed herein.

Preferably the first catalyst comprises from about 10% to about 90%, preferably from about 50% to about 80%, and the second catalyst comprises from about 10% to about 60%, preferably from about 20% to about 50%, of the total mass of the first and second catalysts in both of the alkylation zones.

The catalysts are contained in a fixed-bed system or a moving-bed system with associated continuous catalyst regeneration whereby catalyst may be continuously withdrawn, regenerated and returned to the reactors. These alternatives are associated with catalyst-regeneration options known to those of ordinary skill in the art, such as: (1) a semi-regenerative unit containing fixed-bed reactors maintains operating severity by increasing temperature, eventually shutting the unit down for catalyst regeneration and reactivation; (2) a swing-reactor unit, in which individual fixed-bed reactors are serially isolated by manifolding arrangements as the catalysts become deactivated and the catalyst in the isolated reactor is regenerated and reactivated while the other reactors remain on-stream; (3) continuous regeneration of catalyst withdrawn from a moving-bed reactor, with reactivation and return to the reactors of the reactivated catalyst as described herein; or: (4) a hybrid system with semi-regenerative and continuous-regeneration provisions in the same zone. The preferred embodiment of the process disclosed herein is a fixed-bed semi-regenerative system. In one embodiment of the fixed-bed semi-regenerative system, a fixed-bed UZM-8 alkylation zone is added to an existing fixed-bed semi-regenerative beta alkylation process unit to process streams upstream of the beta alkylation zone and enhance the yield, activity-stability, and/or yield stability obtained in the semi-regenerative system.

The most widely practiced hydrocarbon conversion processes to which this disclosure is applicable are the catalytic alkylation of benzene with ethylene to produce ethylbenzene, the catalytic alkylation of benzene with propylene to produce cumene, and the catalytic alkylation of benzene with butene to produce butylbenzene. Although the discussion herein will occasionally refer to a catalytic ethylbenzene reaction system, the discussion mainly is in reference to its application to a catalytic cumene reaction system. It is not intended that this discussion limit the scope of this disclosure as set forth in the claims.

The catalyst used in the first of the sequential alkylation zones of the process disclosed herein contains one or more members of the family of aluminosilicate and substituted aluminosilicate zeolites designated UZM-8. U.S. Pat. No. 6,756,030, incorporated herein by reference, describes UZM-8 and its preparation, and therefore it is not necessary herein to describe these in detail. Briefly, UZM-8 zeolites are prepared in an alkali-free reaction medium in which only one or more organoammonium species are used as structure directing agents. In this case, the microporous crystalline zeolite (UZM-8) has a composition in the as-synthesized form and on an anhydrous basis expressed by the empirical formula:

$$R_r^{p+}Al_{1-x}E_xSi_yO_z$$

where R is at least one organoammonium cation selected from the group consisting of protonated amines, protonated diamines, quaternary ammonium ions, diquaternary ammonium ions, protonated alkanolamines and quaternized alkanolammonium ions. Preferred organoammonium cations are those that are non-cyclic or those that do not contain a cyclic group as one substituent. Of these, those that contain at least two methyl groups as substituents are especially preferred. Examples of preferred cations include without limitation DEDMA, ETMA, HM and mixtures thereof. The ratio of R to (Al+E) is represented by "r" which varies from about 0.05 to about 5. The value of "p" which is the weighted average valence of R varies from 1 to about 2. The ratio of Si to (Al+E) is represented by "y" which varies from about 6.5 to about 35. E is an element which is tetrahedrally coordinated, is present in the framework and is selected from the group consisting of gallium, iron, chromium, indium and boron. The mole fraction of E is represented by "x" and has a value from 0 to about 0.5, while "z" is the mole ratio of O to (Al+E) and is given by the equation $$z=(r\cdot p+3+4\cdot y)/2$$

The UZM-8 zeolites can be prepared using both organoammonium cations and alkali and/or alkaline earth cations as structure directing agents. As in the alkali-free case above, the same organoammonium cations can be used here. Alkali or alkaline earth cations are observed to speed up the crystallization of UZM-8, often when present in amounts less than 0.05 M<sup>-</sup>/Si. For the alkali and/or alkaline earth metal containing systems, the microporous crystalline zeolite (UZM-8) has a composition in the as-synthesized form and on an anhydrous basis expressed by the empirical formula:

$$M_m^{n+}R_r^{p+}Al_{1-x}E_xSi_yO_z$$

where M is at least one exchangeable cation and is selected from the group consisting of alkali and alkaline earth metals. Specific examples of the M cations include but are not limited to lithium, sodium, potassium, rubidium, cesium, calcium, strontium, barium and mixtures thereof. Preferred R cations include without limitation DEDMA, ETMA, HM and mixtures thereof. The value of "m" which is the ratio of M to (Al+E) varies from about 0.01 to about 2. The value of "n" which is the weighted average valence of M varies from about 1 to about 2. The ratio of R to (Al+E) is represented by "r" which varies from 0.05 to about 5. The value of "p" which is the weighted average valence of R varies from about 1 to about 2. The ratio of Si to (Al+E) is represented by "y" which varies from about 6.5 to about 35. E is an element which is tetrahedrally coordinated, is present in the framework and is selected from the group consisting of gallium, iron, chromium, indium and boron. The mole fraction of E is represented by "x" and has a value from 0 to about 0.5, while "z" is the mole ratio of O to (Al+E) and is given by the equation $$z=(m\cdot n+r\cdot p+3+4\cdot y)/2$$

where M is only one metal, then the weighted average valence is the valence of that one metal, i.e. +1 or +2. However, when more than one M metal is present, the total amount of $$M_m^{n+}=M_{m1}^{(n1)+}+M_{m2}^{(n2)+}+M_{m3}^{(n3)+}+\ldots$$

and the weighted average valence "n" is given by the equation:

$$n = \frac{m_1 \cdot n_1 + m_2 \cdot n_2 + m_3 \cdot n_3 + \ldots}{m_1 + m_2 + m_3 \ldots}$$

Similarly when only one R organic cation is present, the weighted average valence is the valence of the single R cation, i.e., +1 or +2. When more than one R cation is present, the total amount of R is given by the equation.

$$R_r^{p+}=R_{r1}^{(p1)+}+R_{r2}^{(p2)+}+R_{r3}^{(p3)+}$$

and the weighted average valence "p" is given by the equation $$p = \frac{p_1 \cdot r_1 + p_2 \cdot r_2 + p_3 \cdot r_3 + \ldots}{r_1 + r_2 + r_3 + \ldots}$$

The microporous crystalline zeolites used in the first alkylation zone of the process disclosed herein are prepared by a hydrothermal crystallization of a reaction mixture prepared by combining reactive sources of R, aluminum, silicon and optionally M and E. The sources of aluminum include but are not limited to aluminum alkoxides, precipitated aluminas, aluminum metal, sodium aluminate, organoammonium aluminates, aluminum salts and alumina sols. Specific examples of aluminum alkoxides include, but are not limited to aluminum ortho sec-butoxide and aluminum ortho isopropoxide. Sources of silica include but are not limited to tetraethylorthosilicate, colloidal silica, precipitated silica, alkali silicates and organoammonium silicates. A special reagent consisting of an organoammonium aluminosilicate solution can also serve as the simultaneous source of Al, Si, and R. Sources of the E elements include but are not limited to alkali borates, boric acid, precipitated gallium oxyhydroxide, gallium sulfate, ferric sulfate, ferric chloride, chromium nitrate and indium chloride. Sources of the M metals include the halide salts, nitrate salts, acetate salts, and hydroxides of the respective alkali or alkaline earth metals. R can be introduced as an organoammonium cation or an amine. When R is a quaternary ammonium cation or a quaternized alkanolammonium cation, the sources include but are not limited the hydroxide, chloride, bromide, iodide and fluoride compounds. Specific examples include without limitation diethyldimethylammonium (DEDMA) hydroxide, ethyltrimethylammonium (ETMA) hydroxide, tetramethylammonium hydroxide, tetraethylammonium hydroxide, hexamethonium bromide, tetrapropylammonium hydroxide, methyltriethylammonium hydroxide, DEDMA chloride, tetramethylammonium chloride and choline chloride. R may also be introduced as an amine, diamine, or alkanolamine that subsequently hydrolyzes to form an organoammonium cation. Specific non-limiting examples are N,N,N',N'-tetramethyl-1,6-hexanediamine, triethylamine, and triethanolamine. Preferred sources of R without limitation are ETMAOH, DEDMAOH, and hexamethonium dihydroxide $(HM(OH)_2)$.

The reaction mixture containing reactive sources of the desired components can be described in terms of molar ratios of the oxides by the formula:

$$aM_{2/n}O:bR_{2/p}O:1-cAl_2O_3:cE_2O_3:dSiO_2:eH_2O$$

where "a" varies from 0 to about 25, "b" varies from about 1.5 to about 80, "c" varies from 0 to 1.0, "d" varies from about 10 to about 100, and "e" varies from about 100 to about 15000. If alkoxides are used, it is preferred to include a distillation or evaporative step to remove the alcohol hydrolysis products. The reaction mixture is now reacted at a temperature of about 85° C. to about 225° C. (185 to 437° F.) and preferably from about 125° C. to about 150° C. (257 to 302° F.) for a period of about 1 day to about 28 days and preferably for a time of about 4 days to about 14 days in a sealed reaction vessel under autogenous pressure. After crystallization is complete, the solid product is isolated from the heterogeneous mixture by means such as filtration or centrifugation, and then washed with deionized water and dried in air at ambient temperature up to about 100° C. (212° F.).

The UZM-8 aluminosilicate zeolite, which is obtained from the above-described process, is characterized by an x-ray diffraction pattern, having at least the d-spacings and relative intensities set forth in Table A below:

TABLE A d-Spacings and Relative Intensities for as-synthesized UZM-8

| 2-θ | d(Å) | $I/I_0$ % |
|---|---|---|
| 6.40-6.90 | 13.80-12.80 | w-s |
| 6.95-7.42 | 12.70-11.90 | m-s |
| 8.33-9.11 | 10.60-9.70 | w-vs |
| 19.62-20.49 | 4.52-4.33 | m-vs |
| 21.93-22.84 | 4.05-3.89 | m-vs |
| 24.71-25.35 | 3.60-3.51 | w-m |
| 25.73-26.35 | 3.46-3.38 | m-vs |

The UZM-8 compositions are stable to at least 600° C. (1112° F.) (and usually at least 700° C. (1292° F.)). The characteristic diffraction lines associated with typical calcined UZM-8 samples are shown below in table B. The as-synthesized form of UZM-8 is expandable with organic cations, indicating a layered structure.

TABLE B d-Spacings and Relative Intensity for Calcined UZM-8

| 2-θ | d(Å) | $I/I_0$ % |
|---|---|---|
| 4.05-4.60 | 21.80-19.19 | w-m |
| 7.00-7.55 | 12.62-11.70 | m-vs |
| 8.55-9.15 | 10.33-9.66 | w-vs |
| 12.55-13.15 | 7.05-6.73 | w |
| 14.30-14.90 | 6.19-5.94 | m-vs |
| 19.55-20.35 | 4.54-4.36 | w-m |
| 22.35-23.10 | 3.97-3.85 | m-vs |
| 24.95-25.85 | 3.57-3.44 | w-m |
| 25.95-26.75 | 3.43-3.33 | m-s |

An aspect of the UZM-8 synthesis that contributes to some of its unique properties is that it can be synthesized from a homogenous solution. In this chemistry, soluble aluminosilicate precursors condense during digestion to form extremely small crystallites that have a great deal of external surface area and short diffusion paths within the pores of the crystallites. This can affect both adsorption and catalytic properties of the material.

As-synthesized, the UZM-8 material will contain some of the charge balancing cations in its pores. In the case of syntheses from alkali or alkaline earth metal-containing reaction mixtures, some of these cations may be exchangeable cations that can be exchanged for other cations. In the case of organoammonium cations, they can be removed by heating under controlled conditions. In the cases where UZM-8 is prepared in an alkali-free system, the organoammonium cations are best removed by controlled calcination, thus generating the acid form of the zeolite without any intervening ion-exchange steps. The controlled calcination conditions include the calcination conditions described herein below for the composite catalyst, and it may sometimes be possible desirable to perform the controlled calcination of the zeolite after the zeolite has been combined with a binder. On the other hand, it may sometimes be possible to remove a portion of the organoammonium via ion exchange. In a special case of ion exchange, the ammonium form of UZM-8 may be generated via calcination of the organoammonium form of UZM-8 in an ammonia atmosphere.

The catalyst used in the first alkylation zone of the process disclosed herein preferably contains calcined UZM-8. Calcination of as-synthesized UZM-8 effects changes such as in the x-ray diffraction pattern. The UZM-8 zeolite used in the catalyst used in the process disclosed herein contains preferably less than 0.1 wt %, more preferably less than 0.05 wt %, and even more preferably less than 0.02 wt % of alkali and alkaline earth metals.

The catalyst used in the second of the sequential alkylation zones of the process disclosed herein contains zeolite beta, which is well known to those skilled in the art. Suitable zeolite betas include, but are not limited to, the naturally occurring mixture of the three polytypes, any one of the three polytypes, or any combination of the three polytypes. Suitable zeolite betas is also include pristine zeolite beta in which the $H^+$ ion has at least partially replaced the contained metal cation and zeolite beta into which certain quantities of alkaline, alkaline-earth, or metallic cations have been introduced by ion exchange. Various modifications of zeolite beta are also suitable for purposes of this disclosure. Suitable modified zeolite betas include, but are not limited to, zeolite beta which has been modified by steam treatment and ammonium ion treatment and zeolite beta in which the $H^+$ ion has at least partially replaced the contained metal cation, with the zeolite beta being modified by isomorphous substitution of aluminum by boron, gallium, or iron. It is believed that suitable zeolites for use in accordance with this disclosure also include zeolites that are synthesized by modified preparation methods, such as, but not limited to, a preparation method comprising forming a reaction mixture comprising water, a source of silicon dioxide, a source of fluoride ions, a source of tetraethylammonium cations, and, optionally, a source of an oxide of a trivalent element. One zeolite beta suitable for use in alkylation in accordance with this disclosure is disclosed in U.S. Pat. No. 5,723,710, the teachings of which are incorporated herein by reference. This preferred zeolite is a surface-modified zeolite beta which results from acid washing of a templated native zeolite beta. The teachings of U.S. Pat. No. 4,891,458; U.S. Pat. No. 5,081,323; and U.S. Pat. No. 5,522,984 are also incorporated herein by reference. For use in the process disclosed herein, the zeolite used in either or both of the sequential alkylation zones preferably is mixed with a binder for convenient formation of catalyst particles in a proportion of about 5 to 100 mass % zeolite and 0 to 95 mass-% binder, with the zeolite preferably comprising from about 10 to 90 mass-% of the composite. The binder should preferably be porous, have a surface area of about 5 to about 800 m$^2$/g, and be relatively refractory to the conditions utilized in the hydrocarbon conversion process. Non-limiting examples of binders are aluminas, titania, zirconia, zinc oxide, magnesia, boria, silica-alumina, silica-magnesia, chromia-alumina, alumina-boria, silica-zirconia, etc.; silica, silica gel, and clays. Preferred binders are amorphous silica and alumina, including gamma-, eta-, and theta-alumina, with gamma- and eta-alumina being especially preferred.

The zeolite used in either or both of the sequential alkylation zones, with or without a binder, can be formed into various shapes such as pills, pellets, extrudates, spheres, etc. Preferred shapes are extrudates and spheres. Extrudates are prepared by conventional means which involves mixing of zeolite either before or after adding metallic components, with the binder and a suitable peptizing agent to form a homogeneous dough or thick paste having the correct moisture content to allow for the formation of extrudates with acceptable integrity to withstand direct calcination. The dough then is extruded through a die to give the shaped extrudate. A multitude of different extrudate shapes are possible, including, but not limited to, cylinders, cloverleaf, dumbbell and symmetrical and asymmetrical polylobates. It is also within the scope of this disclosure that the extrudates may be further shaped to any desired form, such as spheres, by any means known to the art.

Spheres can be prepared by the well known oil-drop method which is described in U.S. Pat. No. 2,620,314, which is hereby incorporated herein by reference. The method involves dropping a mixture of zeolite, and for example, alumina sol, and gelling agent into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 50-200° C. (122-392° F.) and subjected to a calcination procedure at a temperature of about 450-700° C. (842-1292° F.) for a period of about 1 to about 20 hours. This treatment effects conversion of the hydrogel to the corresponding alumina matrix.

The catalyst composite is dried at a temperature of from about 100° to about 320° C. (212 to 608° F.) for a period of from about 2 to about 24 or more hours and, usually, calcined at a temperature of from 400° to about 650° C. (752 to 1202° F.) in an air atmosphere for a period of from about 1 to about 20 hours. The calcining in air may be preceded by heating the catalyst composite in nitrogen to the temperature range for calcination and holding the catalyst composite in that temperature range for from about 1 to about 10 hours.

The binder used in the catalyst composite for the first sequential alkylation zone of the process disclosed herein preferably contains less alkali and alkaline earth metals than the UZM-8, and more preferably contains little or no alkali and alkaline earth metals. Therefore, the catalyst composite for the first sequential alkylation zone has a content of alkali and alkaline earth metals of less than that of the UZM-8 zeolite used in forming the catalyst composite, owing to the binder effectively lowering the alkali and alkaline earth metals content of the catalyst composite as a whole.

The catalyst used in the first alkylation zone can comprise not only the above-described UZM-8 zeolite but also the above-described beta zeolite; however the first alkylation catalyst preferably comprises more of the UZM-8 zeolite than the beta zeolite. In another alternative, the catalyst used in the second alkylation zone can comprise not only the beta zeolite but also the UZM-8 zeolite; however the second alkylation catalyst preferably comprises more of the beta zeolite than the UZM-8 zeolite. When either catalyst contains more than one zeolite, the mixed catalyst may be produced by physically mixing the different zeolite components prior to forming the catalyst particles or by physically mixing catalyst particles containing one zeolite with other catalyst particles containing another zeolite. An example of the former method of preparing a mixed zeolite is to co-mull the two zeolites, normally with a binder to form an extrudable material, and then extruding particles that contain both zeolites.

In the process disclosed herein, the first alkylation catalyst is preferably located in a position to operate either at a higher olefin concentration, a higher olefin weight hourly space velocity, or both, as compared to the second alkylation catalyst. Therefore the feed olefin is preferably introduced to the first alkylation zone, or where feed olefin is introduced to both the first and second alkylation zones more feed olefin is introduced to the first alkylation zone than to the second alkylation zone. The first alkylation zone is preferably located upstream, with respect to the flow of hydrocarbons, of the second alkylation zone. Without being limited to any particular theory, it is believed that the UZM-8 zeolite is especially selective at producing the desired monoalkylated aromatic when the concentration of olefin is relatively high.

The first and second alkylation zones are preferably in a sequential arrangement. At least a portion of the effluent of the first alkylation zone passes to the second alkylation zone. In one embodiment, the effluent of the second alkylation zone passes to product separation facilities for recovering the monoalkylated aromatic. Such product separation facilities generally comprise one or more fractionation zones for recovering fractions from the second effluent. For example, in a cumene process the product separation facilities zone generally comprise a benzene fractionation column to recover unreacted benzene for recycle to the alkylation zone; a cumene fractionation column to recover product cumene from heavier polyalkylbenzenes; an optional polyalkylbenzene fractionation column to separate DIPBs and TIPBs from other heavier components. The product separation facilities may comprise a depropanizer if the concentrations of unreacted propylene, propane, or light $C_3$-minus paraffins in the second zone effluent are high enough to justify their separation. The product separation facilities thus produces a fraction comprising monoalkylated aromatic as well as other fractions, and some or all of at least one of these other fractions recovered from the product separation facilities can be recycled to the first alkylation zone, the second alkylation zone, or both. In cumene production, for example, the recovered fractions that are recycled preferably comprise benzene, polyisopropylbenzenes, or both. Unless otherwise noted in this specification, the term "portion"—when describing a process stream—refers to either an aliquot portion of the stream or a dissimilar fraction of the stream having a different composition than the total stream from which it was derived. An aliquot portion of the stream is a portion of the stream that has essentially the same composition as the stream from which it was derived.

In one embodiment, the two alkylation zones are in a sequential arrangement, feed aromatic and feed olefin are charged to the first alkylation zone, which contains UZM-8 catalyst. An aliquot portion of the alkylation effluent of the second alkylation zone, which contains beta catalyst, is recycled to the first alkylation zone containing UZM-8 catalyst. At least in theory, the aliquot portion of the second zone effluent can be recycled at a rate that is limited only by economic considerations. Except for the aliquot portion of the second zone effluent that is passed downstream to product separation facilities, the second zone effluent is available for recycle in what amounts to an unlimited quantity. Any feed aromatic or feed olefin in the first alkylation zone effluent is charged to the second alkylation zone. Additional feed aromatic and/or feed olefin can be also charged to the second alkylation zone at a point downstream of the first alkylation zone, but preferably no additional feed olefin is charged to the second alkylation zone.

In another embodiment, the two alkylation zones are in a sequential arrangement, an alkylbenzene column in the product separation facilities produces a bottom stream, and this bottom stream is recycled to the first alkylation zone, which contains UZM-8 catalyst. The bottom stream of the alkylbenzene column contains a relatively low concentration of alkylbenzene (e.g., cumene) and a relatively high concentration of polyalkylbenzenes (e.g., DIPBs and TIPBs). An aliquot portion of the effluent of the second alkylation zone, which contains beta catalyst, may also be recycled to the first alkylation zone.

In another embodiment, an olefin stream is admixed with a feed aromatic stream and with a cooled aliquot portion of the effluent of the first alkylation zone. The admixture enters the first alkylation zone and contacts the catalyst comprising UZM-8 zeolite. The first alkylation zone effluent divides into two aliquot portions. One aliquot portion passes to the second alkylation zone containing beta catalyst. The other aliquot portion of the first alkylation zone effluent stream is cooled by exchanging heat indirectly with boiler feed water to produce steam, and then combines to form the admixture fed to the first alkylation zone.

In another embodiment, two alkylation reactors are in a sequential arrangement, and each reactor contains two beds of UZM-8 zeolite catalyst that are also in a sequential arrangement. Feed aromatic is charged to the first bed of the first alkylation reactor and feed olefin is charged to each of the beds. The effluent of the first alkylation reactor is cooled in a heat exchanger and flows to the second alkylation reactor. The effluent of the second alkylation reactor divides into two aliquot portions. One aliquot portion flows to a downstream alkylation reactor containing beta catalyst. The other aliquot portion is cooled in a heat exchanger and divides into two aliquot portions. One aliquot flows to the first alkylation reactor and the other aliquot portion flows to the second alkylation zone containing beta zeolite catalyst.

In another embodiment, two alkylation reactors are in a sequential arrangement, each alkylation reactor contains a pair of beds of UZM-8 zeolite catalyst, and each of the two beds in a pair are also in a sequential arrangement. Feed aromatic is charged to the first bed of the first alkylation reactor and feed olefin is charged to each of the beds. The effluent of the first alkylation reactor is cooled in a heat exchanger and flows to the second alkylation reactor. The effluent of the second alkylation reactor divides into two aliquot portions. One aliquot portion flows to a downstream alkylation reactor containing beta catalyst. The other aliquot portion is cooled in a heat exchanger and divides into two aliquot portions. One aliquot portion flows to the first bed of the first alkylation reactor and the other aliquot portion flows to the first bed of the second alkylation reactor.

In another embodiment, a transalkylation reactor and a first alkylation reactor are in a sequential arrangement. Polyalkylbenzenes and benzene enter any suitable transalkylation reactor and contact any suitable transalkylation catalyst, such as the Y-containing catalysts to form alkylbenzene. The transalkylation reactor effluent is optionally heated or cooled and flows to the first alkylation reactor. The first alkylation reactor contains two beds of UZM-8 zeolite catalyst in a sequential arrangement, and feed olefin is charged to each bed. The effluent of the first alkylation reactor divides into two aliquot portions. One aliquot portion flows to a second alkylation reactor containing beta zeolite catalyst, and the other aliquot portion is cooled in a heat exchanger and flows to the first bed of the alkylation reactor. The effluent of the second alkylation reactor flows to product separation facilities. Optionally, an aliquot portion of the second alkylation reactor effluent may be recycled to either or both beds of the first alkylation reactor and/or to the second alkylation reactor.

In another embodiment, an alkylation reactor contains four catalyst beds in a sequential arrangement. Feed olefin and feed aromatic are charged to the first bed, which can contain any suitable alkylation catalyst. The effluent of the first bed flows to the second bed, which contains a UZM-8 zeolite catalyst. Additional feed olefin is charged to the second bed. The effluent of the second bed is charged to the third bed, which can contain any suitable alkylation catalyst, such as those described for use in the first bed. Optionally, additional feed olefin is charged to the third bed. The effluent of the third bed passes to a fourth bed containing beta zeolite catalyst, and no additional olefin is charged to the fourth bed. The effluent of the fourth bed is withdrawn from the alkylation reactor and divides into two aliquot portions. One aliquot portion flows to a downstream alkylation reactor or to product separation facilities, and the other aliquot portion is cooled in a heat exchanger and flows to one or more of the bed of the alkylation reactor.

In another embodiment, two alkylation reactors are in a sequential arrangement, the first alkylation reactor contains a pair of beds of UZM-8 zeolite catalyst, the second alkylation reactor contains a pair of beds of beta zeolite catalyst, and each of the two beds in a pair are also in a sequential arrangement. Feed aromatic is charged to the first bed of the first alkylation reactor and feed olefin is charged to each of the beds in the first alkylation reactor. The effluent of the first alkylation reactor is cooled in a heat exchanger and flows with additional feed olefin to the second alkylation reactor. The effluent of the second alkylation reactor flows to a fractionation column, such as a deethanizer or a depropanizer or a debutanizer to remove lighter hydrocarbons from the second alkylation reactor effluent. These lighter hydrocarbons can be ethane and lighter compounds when producing ethylbenzene, propane and lighter compounds when producing cumene, and butane and lighter compounds when producing butylbenzenes. The bottom stream of this fractionation column divides into two aliquot portions. One aliquot portion flows to product separation facilities. The other aliquot portion is optionally cooled in a heat exchanger and divides into two aliquot portions. One aliquot portion flows to the first bed of the first alkylation reactor and the other aliquot portion flows to the first bed of the second alkylation reactor.

Optionally, for each of the embodiments described herein, a portion of the effluent from the first alkylation zone may be recycled to the first alkylation zone, a portion of the effluent from the second alkylation zone may be recycled to the second alkylation zone, and/or a portion of the effluent from the second alkylation zone may be recycled to the first alkylation zone. In addition, for each embodiment, a fractionation column may optionally be used to recover feed aromatic, such as benzene, as an overhead stream from a portion of the first zone effluent, a portion of the second zone effluent, or both for recycle to the first zone, the second zone, or both zones. Preferably, the feed aromatic is introduced to the second zone, so that the first zone operates at a lower molar ratio of aryl groups per phenyl group than the second zone. In addition, any of the feed olefins disclosed herein, such as ethylene, propylene, or butanes, and any of the feed aromatics, such as benzene, may be used in any embodiment.

Alkylation conditions for the first and second alkylation zones include a molar ratio of aryl groups per alkyl group of generally from 25 to about 1. The molar ratio may be less than 1, and it is believed that the molar ratio may be 0.75 or lower. The molar ratio of aryl groups per alkyl group may be the same in both the first and second alkylation zones. Alternatively the molar ratio may be higher in the second alkylation zone than in the first alkylation zone. A higher ratio can be attained by, for example, introducing feed aromatic between the first and second alkylation zones. Since introducing feed olefin into a reaction zone would tend to decrease this molar ratio, it is preferred to not add additional feed olefin between the first and second alkylation zones or into the second alkylation zone. However, given the need to control the heat of reaction and delta temperature that results from processing a high olefin concentration at low molar ratio, it may be necessary from a practical standpoint to distribute the introduction of the olefin feed amongst the various alkylation catalyst beds Also, since introducing dialkylated aromatics or trialkylated aromatics into an alkylation zone intended to produce monoalkylated aromatics (e.g., introducing DIPBs or TIPBs into an alkylation reaction zone for producing cumene) would tend to decrease this molar ratio, it is preferred that such additional polyalkylated aromatics not be added to the second alkylation zone.

Where a portion of an alkylation zone effluent is recycled to the same alkylation zone, the ratio of the weight of the recycled portion of the effluent entering the alkylation zone per unit time to the sum of the weights entering the alkylation catalyst zone of the feed aromatic and the feed olefin per the unit time may be at least 0.1, at least 1.0, at least 2.5, at least 4.0, at least 7.0, or at least 10.0. This ratio is sometimes referred to herein as the effluent recycle ratio or R/FF. Where a portion of the second alkylation zone effluent is recycled to the first alkylation zone, the ratio of the weight of the recycled portion of the second alkylation zone effluent entering the first alkylation zone per unit time to the sum of the weights entering the first alkylation zone of the feed aromatic and the feed olefin per the unit time may be at least 0.1, at least 1.0, at least 2.5, at least 4.0, at least 7.0, or at least 10.0.

In general, for a given molar ratio of alkylation substrate per alkylation agent, especially an olefinic alkylation agent, the greater the molar ratio of aryl groups to alkyl group in the feed stream, the less is the rise in temperature in the alkylation zone that occurs as a result of the alkylation reactions. The alkylation reactions are considered to be moderately exothermic. Although an alkylation zone, an alkylation reactor, and/or an alkylation catalyst bed may have indirect heat exchange means to remove the heat as it is produced, each zone, reactor, or bed is preferably adiabatic, and so the outlet temperature of the effluent stream is higher than the inlet temperature of the reactants. An increase in R/FF, as well as an increase in the molar ratio of aryl groups to alkyl groups in the feed stream, increases the quantity of aryl groups available to act as a heat sink in the alkylation zone and thus decreases the temperature rise in the alkylation zone. While in practicing the process disclosed herein, the appropriate alkylation temperature may be generally from 60° C. (140° F.) to the critical temperature of the alkylation substrate, which may be 475° C. (887° F.) or even higher, the inlet temperature in the alkylation zone is generally from 60 to 260° C. (140 to 500° F.), and preferably from 100 to 250° C. (212 to 482° F.). Although the temperature rise that occurs in the alkylation zone could be from 10 to 190° C. (18 to 342° F.) depending on the total mass flows in the alkylation zone, the temperature rise is generally from 5 to 130° C. (9 to 234° F.), and preferably from 5 to 50° C. (9 to 90° F.).

As described previously, the temperature rise in the alkylation zone may be controlled by adjusting the molar ratio of aryl groups to alkyl group in the feed stream. Minimizing the temperature rise helps prevent high reactor outlet temperatures, which cause undesirable side reactions, such as isomerization of aromatic side-chains leading to compounds such as n-propylbenzene and heavy aromatic formation, to occur. High alkylation temperatures can also cause vaporization of benzene and the desired monoalkylaromatic (e.g. ethylbenzene or cumene) in the alkylation zone. In one embodiment of the process disclosed herein, the temperature rise in the alkylation zone can be controlled by withdrawing an effluent stream from the alkylation reaction zone, optionally cooling a portion of the effluent stream, and recycling the cooled portion of the effluent stream to the reaction zone.

Alkylation in both alkylation zones is preferably performed in the liquid phase. Consequently, alkylation pressures preferably are sufficiently high to ensure at least a partial liquid phase. The pressure range for the reactions is usually from about 1379 to 6985 kPa(g) (200 to about 1000 psi(g)), more commonly from about 2069 to 4137 kPa(g) (300 to about 600 psi(g)), and even more commonly from about 3103 to 4137 kPa(g) (450 to about 600 psi(g)). Preferably, the alkylation conditions are sufficient to maintain benzene in a liquid phase and are supercritical conditions for propylene.

The weight hourly space velocity (WHSV) of the feed olefin may range from 0.01 to 8.0 $hr^{-1}$. As used herein, weight hourly space velocity of a component means the weight flow rate of the component per hour divided by the catalyst weight, where the weight flow rate of the component per hour and the catalyst weight are in the same weight units. Preferably, the WHSV of the feed olefin is higher in the first alkylation zone than in the second alkylation zone. The WHSV of the feed olefin may preferably range from 0.5 to 2.0 $hr^{-1}$ in the first alkylation zone and from 0.1 to 1.0 $hr^{-1}$ in the second alkylation zone. The WHSV of aromatics is generally from 0.3 to 480 $hr^{-1}$ in both alkylation zones.

In the context of aromatic alkylation, the principal reaction that occurs in the first and second alkylation zone is the alkylation of the feed aromatic by the feed olefin to produce a monoalkylated aromatic. In addition, other side reactions can occur also in the first and/or second reaction zone. For example, the feed aromatic can transalkylate with a polyalkylated aromatic to produce the monoalkylated aromatic. Also, the polyalkylated aromatic can be alkylated with the feed olefin. The effluent stream of each reaction zone thus may contain monoalkylated aromatic, polyalkylated aromatic that was either charged to the alkylation zone or was a byproduct of a side reaction, feed aromatic that was either charged to the alkylation zone or is the byproduct of a side reaction, feed olefin at low concentration, and $C_1$ to $C_3$ paraffins.

The following examples illustrate the process disclosed herein.

Example 1

An aluminosilicate reaction mixture was prepared in the following manner. A 7329.73 g portion of DEDMAOH (20% aq) was added to a tank. A 804.38 g portion of Al (Osec-Bu)$_3$ (95%+) was added to the tank, and the resulting solution was thoroughly mixed for 45 min. A 2000 g quantity of deionized water was then added to the solution, followed by the addition of a 2526.96 g portion of precipitated silica (Ultrasil™ VN SP3, 89% SiO$_2$). Next, a solution of 126.69 g of NaOH dissolved in 212.25 g of deionized water was prepared and added to the reaction mixture and the reaction mixture was thoroughly mixed for 30 min. The reaction mixture was then transferred to a 19-L stirred reactor. The tank was rinsed with 1000 g of deionized water and the rinse was transferred to the reactor and mixed into the reaction mixture. The reaction mixture was heated in 3 hr to 150° C. and digested at 150° C. for 290 hr. A solid product was collected by filtering, washed with deionized water, and dried at 50° C. The isolated product was identified as UZM-8 by powder x-ray diffraction analysis. Elemental analysis revealed the composition of the isolated product to consist of the elemental mole ratios of Si/Al=11.77, Na/Al=0.26, N/Al=2.03, and C/N=3.04. The isolated product was ammonium ion-exchanged using an ion exchange solution of 1 part by weight of NH$_4$NO$_3$, 10 parts by weight of deionized water, and 1 part by weight of the isolated product at about 75° C. for 3 hr, and the solids were collected by filtering. The ammonium ion exchange and filtration was repeated two more times, and the triple ammonium ion-exchanged material was washed with deionized water and dried at about 50° C. A sample of the dried material was calcined by heating to 540° C. and holding at that temperature for 2 hr in the presence of flowing nitrogen, and then switching to flowing air and holding at that temperature for 14 hr. Thereafter the BET surface area was found to be 481 m$^2$/g and the micropore volume was 0.14 cc/g. Another sample of the dried material was then formulated into a catalyst comprising 70 wt % UZM-8 and 30 wt % alumina. The extrusion was done using HNO$_3$-peptized Al$_2$O$_3$ as a binder and 3.0 wt % based on the weight of the UZM-8 and the alumina of Solka-Floc™ powdered cellulose (BW-40; International Fiber Corp., North Tonawanda, N.Y., USA) as an extrusion aid to obtain 1.6 mm (1/16 in) diameter extrudates. The extrudates were activated in a muffle oven by heating to 538° C. and holding at that temperature for 1 hr in the presence of flowing nitrogen, and then switching to flowing air and holding at that temperature for 15 hr. This catalyst had an average bulk density of 0.48 g/cc. This catalyst is designated as Catalyst A.

A fresh alkylation catalyst comprising 70 wt % zeolite beta and 30 wt % alumina binder was prepared and is designated as Catalyst B. This catalyst had an average bulk density of 0.55 g/cc. The zeolite beta for Catalyst B was prepared in substantially the same manner as described in U.S. Pat. No. 5,522,984.

Example 2

The experimental procedure used in testing the catalysts prepared for Example 1 was as follows. A volume of the catalyst to be tested was loaded into a cylindrical reactor, however for the test of the stacked loading of Catalysts A and B, the bottom 30% of the volume was loaded with Catalyst B and the upper 70% of the volume was loaded with Catalyst A. The reactor was equipped with a thermocouple in a thermowell located to measure temperatures at distances along the length of the fixed catalyst bed. Dry benzene was passed downflow through the reactor at 260° C. (500° F.) and at a benzene LHSV of 6.7 hr$^{-1}$ for 24 hours.

Subsequently, the flow of fresh benzene was adjusted and the reactor inlet temperature was lowered to a temperature about 50° C. (90° F.) below the desired distance average bed temperature (DABT) for the initial testing conditions. As used herein, DABT means the temperature calculated by plotting the catalyst bed temperature versus distance along the catalyst bed, computing the area under the curve from the inlet to the outlet of the catalyst bed, and dividing the area by the length of the catalyst bed. Fresh propylene was introduced into the reactor. Then a portion of the reactor effluent was recycled so that a combined feed of the fresh benzene, the fresh propylene, and the recycled reactor effluent flowed to the reactor. The reactor inlet temperature was adjusted to maintain the desired DABT while the reactor effluent was sampled and analyzed. Then the reactor inlet temperature and/or the amount of recycled reactor effluent was adjusted, and the reactor effluent was sampled again. This process was repeated until measurements and samples were obtained at all of the desired DABTs and effluent recycle ratios (R/FF).

The temperature within the catalyst bed rose as the incoming feed contacted the catalyst due to the exothermic nature of the reaction. At times during a period at test conditions, temperature profiles (bed temperature versus distance through the bed) were plotted. The rate of catalyst deactivation was taken to be the rate of progression of these temperature profiles through the bed. The position of each temperature profile was defined by the end of the active zone, which was a measure of the end of the temperature rise in the temperature profile. On a temperature profile, the end of the active zone was the distance in the bed at the intersection of the linear extrapolation of the linear part of the temperature rise and a horizontal line at the maximum bed temperature. Some catalyst deactivation occurred over the duration that the performance of each catalyst was measured, and it is believed that the deactivation rates of the catalysts were not significantly affected by differences in the operating conditions among the tests of each catalyst.

The DABTs were between about 130° C. (236° F.) and about 160° C. (320° F.) for the tests for Catalyst A alone, about 160° C. (320° F.) and about 175° C. (347° F.) for the tests for Catalyst B alone, and about 150° C. (302° F.) and about 175° C. (347° F.) for the tests of the stacked loading of Catalysts A and B. The propylene WHSV was about 2.03 hr$^{-1}$ for the tests of Catalyst A alone, about 1.88 hr-1 for the tests of Catalyst B alone, and about 1.03 hr-1 for the tests of the stacked loading of Catalysts A and B (or alternatively 1.77 hr-1 for Catalyst A and 2.48 hr-1 for Catalyst B. The molar ratio of fresh benzene to fresh propylene for these tests was about 2. The R/FF for these tests was about 6. Because the molar ratio of aryl groups per propyl group is essentially the same in the combined reactor feed stream and the total reactor effluent stream, the molar ratio of aryl groups per ethyl group is not significantly affected by recycling any portion of the reactor effluent stream.

The results of the tests are shown in Table 3. Each test included almost 600 hours of operation, and the total selectivity to cumene and DIPB and TIPB, and the deactivation rates, reported in Table 3 are determined during the final 525 hours of operation. The average deactivation rate is computed from the location of the end of the active zone after about 50 hours of operation and the location of the end of the active zone after about 575 hours of operation.

TABLE 3

| Catalyst | A | B | 70% A and 30% B |
|---|---|---|---|
| [Pilot Plant/Run No. | 745/409 | 745/396 | 745/411 |
| Selectivity, mol-% | | | |
| Cumene + DIPB + TIPB | 99.8 (High Range) | 99.1 (Low Range) | 100.0 (Even Higher Range) |
| Average deactivation rate, relative distance/unit time | 1.7 (Medium) | 8.9 (High) | 1 (Low) |

These data show the unexpected result that the stacked loading of Catalysts A and B has a selectivity to cumene+DIPB+TIPB that is higher, and an average deactivation rate that is lower, than that of either Catalyst A alone or Catalyst B alone. Without being limited to any particular theory, it is believed that the combination of Catalyst A (UZM-8) and Catalyst B (beta) provides a synergistic effect. It is believed that the UZM-8 catalyst is instrumental in providing the high selectivity and that the beta catalyst is instrumental in providing the low average deactivation rate without adversely affecting the high selectivity.

Example 3

To demonstrate the robustness of the stacked loading of Catalysts A and B to severe and adverse conditions, the test of the stacked loading was continued at various alkylation conditions for an additional approximately 700 hours after the end of the period reported in Example 2. Aside from a relatively insignificant incremental increase in catalyst deactivation, the performances of Catalysts A and B in the stacked loading were not significantly affected by this additional operation. During the final 77 hours (Period I) of this additional operation, the operating conditions of the stacked catalyst loading were lined out at a reactor inlet temperature of 109° C. (228° F.), a propylene WHSV of about 1.03 hr$^{-1}$, a molar ratio of fresh benzene to fresh propylene of about 2, and a R/FF of about 6. The concentration of water in the combined feed (i.e., fresh benzene, fresh propylene, and reactor effluent recycle) was less than 5 wt-ppm.

To simulate the effect of high water contamination of the feed, water was introduced after Period I to obtain a water concentration in the combined feed of about 150 wt-ppm for about 62 hours (Period II). While maintaining this high water concentration in the combined feed, the inlet temperature was set at 113° C. (235° F.) for about 41 hours (Period III), then at 118° C. (244° F.) for about 23 hours (Period IV), and then at 128° C. (262° F.) for about 90 hours (Period V). Following period V, the plant was shutdown without unloading the catalyst. Prior to resuming propylene introduction to the reactor, benzene having a water concentration of about 150 wt-ppm was circulated through the stacked catalyst loading at an elevated temperature (i.e., between about 100° C. (212° F.) and 128° C. (262° F.) for more than 112 hrs. The plant was restarted on a combined feed having a water concentration of less than 5 wt-ppm, a propylene WHSV of about 1.03 hr$^{-1}$, a molar ratio of fresh benzene to fresh propylene of about 2, and a R/FF of about 6. The reactor inlet temperature was set at 128° C. (262° F.) for about 14 hours (Period VI), then at 118° C. (244° F.) for about 42 hours (Period VII), and then at 108° C. (226° F.) for about 45 hours (Period VIII).

The performance of the stacked loading is shown in Table 4. These data indicate that unexpectedly good performance can be achieved with a stacked loading of UZM-8 and beta catalysts, despite a high water contamination that caused a large drop in propylene conversion from 97% to 75% between Periods I and II. By increasing the reactor inlet temperature from of 109° C. (228° F.) in Period II to 128° C. (262° F.) in Period V, propylene conversion was increased during Period V prior to the shutdown to 93%, or nearly the level achieved during Period I, without a significant decrease in the total selectivity to cumene and DIPB and TIPB or a significant increase in the selectivity to TIPB or to the byproduct nPB. Furthermore, the data after the restart during Periods VI-VIII indicate that the contaminating effect of water can be reversed and the reactor by returning to a relatively dry feed, despite the occurrence of an intervening shutdown. The inlet temperature was lowered from 128° C. (262° F.) in Period VI to 108° C. (226° F.) in Period VIII, while maintaining 97% olefin conversion, 99.67 to 99.72 mol-% selectivity to cumene+DIPB+TIPB and while decreasing the nPB/cumene ratio to 132.

TABLE 4

[Pilot Plant 745, Run 411]

| Period | Inlet, ° C. (° F.) | Water in combined feed, wt-ppm | Propylene Conversion, mol-% | nPB/ Cumene, wt-ppm/ wt-ppm | Selectivity to Cumene + DIPB + TIPB, mol-% | Selectivity to TIPB, mol-% |
|---|---|---|---|---|---|---|
| I | 109 (228) | <5 | 97 | 132 | 99.66 | 2.6 |
| II | 109 (228) | 150 | 75 | 118 | 99.53 | 2.62 |
| III | 113 (235) | 150 | 79 | 123 | 99.55 | 2.64 |
| IV | 118 (244) | 150 | 85 | 148 | 99.57 | 2.63 |
| V | 128 (262) | 150 | 93 | 186 | 99.59 | 2.74 |
| VI | 128 (262) | <5 | 97 | 200 | 99.72 | 2.1 |
| VII | 118 (244) | <5 | 97 | 160 | 99.7 | 2.41 |
| VIII | 108 (226) | <5 | 97 | 132 | 99.67 | 2.98 |

The invention claimed is:

1. A process for the catalytic alkylation of an aromatic substrate with an alkylating agent in first and second sequential alkylating zones, the process comprising:
(a) contacting the aromatic substrate and the alkylating agent with a first catalyst in the first alkylation zone to obtain a first effluent, wherein the first catalyst comprises a microporous crystalline zeolite having a layered framework of $AlO_2$ and $SiO_2$ tetrahedral units and a composition on an as-synthesized and anhydrous basis expressed by an empirical formula of:

$$M_m^{n+}R_r^{p+}Al_{1-x}E_xSi_yO_z$$

wherein M is at least one exchangeable cation, "m" is the mole ratio of M to (Al+E) and varies from 0 to about 2, R is at least one organoammonium cation selected from the group consisting of quaternary ammonium cations, diquaternary ammonium cations, protonated amines, protonated diamines, protonated alkanoamines and quaternized alkanolammonium cations, "r" is the mole ratio of R to (Al+E) and has a value of about 0.05 to about 5.0, "n" is the weighted average valence of M and has a value of about 1 to about 2, "p" is the weighted average valence of R and has a value of about 1 to about 2, E is an element selected from the group consisting of gallium, iron, boron, chromium, indium and mixtures thereof, "x" is the mole fraction of E and has a value from 0 to about 1.0, "y" is the mole ratio of Si to (Al+E) and varies from about 6.5 to about 35 and "z" is the mole ratio of O to (Al+E) and has a value determined by the equation:

$$z=(m \cdot n+r \cdot p+3+4 \cdot y)/2;$$

and (b) contacting at least a portion of the first effluent with a second catalyst comprising beta zeolite in the second alkylation zone at second alkylation conditions to obtain a second effluent comprising an alkylaromatic.

2. The process of claim 1 wherein the aromatic substrate is selected from the group consisting of benzene, toluene, and a xylene.

3. The process of claim 1 wherein the alkylating agent is a $C_2$-$C_4$ monoolefin.

4. The process of claim 1 wherein the aromatic substrate is benzene, the alkylating agent is propylene, and the alkylaromatic is cumene.

5. The process of claim 1 wherein the first alkylation conditions comprise a molar ratio of aryl groups to alkyl group of from about 0.75 to about 3.0.

6. The process of claim 1 wherein the first alkylation conditions comprise a molar ratio of the aromatic substrate to the alkylating agent of from about 0.75 to about 3.

7. The process of claim 1 wherein the first alkylation conditions comprise a weight hourly space velocity of the alkylating agent of about 1.0 to about 3.

8. The process of claim 1 wherein the beta zeolite is a surface-modified zeolite beta is characterized by having surface aluminum 2p binding energies as measured by X-ray photoelectron spectroscopy, of at least 74.8 electron volts.

9. A process for the catalytic alkylation of an aromatic substrate with an alkylating agent in first and second sequential alkylating zones, the process comprising:

(a) contacting the aromatic substrate and the alkylating agent with a first catalyst in the first alkylation zone to obtain a first effluent, wherein the first catalyst comprises a microporous crystalline zeolite having a layered framework of $AlO_2$ and $SiO_2$ tetrahedral units and a composition on an as-synthesized and anhydrous basis expressed by an empirical formula of:

$$M_m^{n+}R_r^{p+}Al_{1-x}E_xSi_yO_z$$

wherein M is at least one exchangeable cation, "m" is the mole ratio of M to (Al+E) and varies from 0 to about 2.0, R is at least one organoammonium cation selected from the group consisting of quaternary ammonium cations, diquaternary ammonium cations, protonated amines, protonated diamines, protonated alkanoamines and quaternized alkanolammonium cations, "r" is the mole ratio of R to (Al+E) and has a value of about 0.05 to about 5.0, "n" is the weighted average valence of M and has a value of about 1 to about 2, "p" is the weighted average valence of R and has a value of about 1 to about 2, E is an element selected from the group consisting of gallium, iron, boron, chromium, indium and mixtures thereof, "x" is the mole fraction of E and has a value from 0 to about 1.0, "y" is the mole ratio of Si to (Al+E) and varies from about 6.5 to about 35, and "z" is the mole ratio of O to (Al+E) and has a value determined by the equation:

$$z=(m \cdot n+r \cdot p+3+4 \cdot y)/2$$

and is characterized in that it has the x-ray diffraction pattern having at least the d spacings and intensities set forth in Table A:

TABLE A

| 2-θ | d(Å) | I/I₀ % |
|---|---|---|
| 6.40-6.90 | 13.80-12.80 | w-s |
| 6.95-7.42 | 12.70-11.90 | m-s |
| 8.33-9.11 | 10.60-9.70 | w-vs |
| 19.62-20.49 | 4.52-4.33 | m-vs |
| 21.93-22.84 | 4.05-3.89 | m-vs |
| 24.71-25.35 | 3.60-3.51 | w-m |
| 25.73-26.35 | 3.46-3.38 | m-vs; | and (b) contacting at least a portion of the first effluent with a second catalyst comprising beta zeolite in the second alkylation zone to provide a second effluent comprising an alkylaromatic.

10. The process of claim 9 wherein the aromatic substrate is selected from the group consisting of benzene, toluene, and a xylene.

11. The process of claim 9 wherein the alkylating agent is a $C_2$-$C_4$ monoolefin.

12. The process of claim 9 wherein the aromatic substrate is benzene, the alkylating agent is propylene, and the alkylaromatic is cumene.

13. The process of claim 9 wherein the first alkylation conditions comprise a molar ratio of aryl groups to alkyl group of from about 0.75 to about 3.

14. The process of claim 9 wherein the first alkylation conditions comprise a molar ratio of the aromatic substrate to the alkylating agent of from about 0.75 to about 3.

15. The process of claim 9 wherein the first alkylation conditions comprise a weight hourly space velocity of the alkylating agent of about 1.0 to about 3.

16. The process of claim 9 wherein the contacting in the first alkylation zone is carried out under first alkylation conditions that comprise a concentration of water of from about 1 to about 20000 wt-ppm, based on the weight of hydrocarbon passed to the first alkylation zone.

17. The process of claim 9 wherein the contacting in the second alkylation zone is carried out under second alkylation conditions that comprise a concentration of water of from about 1 to about 20000 wt-ppm, based on the weight of hydrocarbon passed to the second alkylation zone.

18. The process of claim 9 wherein the first alkylation catalyst is UZM-8.

19. The process of claim 9 wherein the beta zeolite is a surface-modified zeolite beta is characterized by having surface aluminum 2p binding energies as measured by X-ray photoelectron spectroscopy, of at least 74.8 electron volts.

20. A process for the catalytic alkylation of benzene with propylene in first and second sequential alkylating zones, the process comprising:

(a) contacting the benzene and propylene with a first catalyst in the first alkylation zone under first alkylation conditions to obtain a first effluent, wherein the first catalyst comprises a microporous crystalline zeolite having a layered framework of $AlO_2$ and $SiO_2$ tetrahedral units and a composition on an as-synthesized and anhydrous basis expressed by an empirical formula of:

$$M_m^{n+}R_r^{p+}Al_{1-x}E_xSi_yO_z$$

wherein M is at least one exchangeable cation, "m" is the mole ratio of M to (Al+E) and varies from 0 to about 2.0, R is at least one organoammonium cation selected from the group consisting of quaternary ammonium cations, diquaternary ammonium cations, protonated amines, protonated diamines, protonated alkanoamines and quaternized alkanolammonium cations, "r" is the mole ratio of R to (Al+E) and has a value of about 0.05 to about 5.0, "n" is the weighted average valence of M and has a value of about 1 to about 2, "p" is the weighted average valence of R and has a value of about 1 to about 2, E is an element selected from the group consisting of gallium, iron, boron, chromium, indium and mixtures thereof, "x" is the mole fraction of E and has a value from 0 to about 1.0, "y" is the mole ratio of Si to (Al+E) and varies from about 6.5 to about 35, and "z" is the mole ratio of 0 to (Al+E) and has a value determined by the equation:

$$z=(m \cdot n + r \cdot p + 3 + 4 \cdot y)/2$$

and is characterized in that it has the x-ray diffraction pattern having at least the d spacings and intensities set forth in Table A:

TABLE A

| 2-θ | d(Å) | I/I₀% |
|---|---|---|
| 6.40-6.90 | 13.80-12.80 | w-s |
| 6.95-7.42 | 12.70-11.90 | m-s |
| 8.33-9.11 | 10.60-9.70 | w-vs |
| 19.62-20.49 | 4.52-4.33 | m-vs |
| 21.93-22.84 | 4.05-3.89 | m-vs |
| 24.71-25.35 | 3.60-3.51 | w-m |
| 25.73-26.35 | 3.46-3.38 | m-vs; | and (b) contacting at least a portion of the first effluent with a second catalyst comprising beta zeolite in the second alkylation zone under second alkylation conditions to obtain a second effluent comprising cumene;

the first and second alkylation conditions comprise a concentration of water of from about 1 to about 20000 wt-ppm, based on the weight of hydrocarbon passed to the first and second alkylation zones respectively.

* * * * *